US00PP24332P2

(12) United States Plant Patent
de Jongh

(10) Patent No.: US PP24,332 P2
(45) Date of Patent: Mar. 25, 2014

(54) *FRAGARIA* PLANT NAMED 'BBB PO 01'

(50) Latin Name: *Fragaria×ananassa*
Varietal Denomination: BBB PO 01

(75) Inventor: Johannes Adrianus Petrus de Jongh, Etten-Leur (NL)

(73) Assignee: Beekers Berries Breeding BV, Made (NL)

( * ) Notice: Subject to any disclaimer, the term of this patent is extended or adjusted under 35 U.S.C. 154(b) by 0 days.

(21) Appl. No.: 13/506,770

(22) Filed: May 16, 2012

(51) Int. Cl.
*A01H 5/00* (2006.01)

(52) U.S. Cl.
USPC ..... Plt./208; Plt./209

(58) Field of Classification Search
USPC ..... Plt./208, 209
See application file for complete search history.

(56) References Cited

PUBLICATIONS

UPOV-PLUTO plant variety database; Mar. 2010; citation for the cultivar 'BBB PO 01'.*

* cited by examiner

*Primary Examiner* — Susan McCormick Ewoldt
(74) *Attorney, Agent, or Firm* — Penny J. Aguirre

(57) ABSTRACT

A new and distinct cultivar of *Fragaria* plant 'BBB PO 01' characterized by its berries that are white with red achenes, firmer than is typical of other cultivars with white colored fruit, very juicy, and highly aromatic with a perfume-like fragrance with a pleasing flavor.

2 Drawing Sheets

Botanical classification: *Fragaria×ananassa.*
Variety denomination: 'BBB PO 01'.

BACKGROUND OF THE INVENTION

The present invention includes a new and distinct cultivar of *Fragaria×ananassa* named 'BBB PO 01', and will herein be referred to as 'BBB PO 01'.

The new variety resulted from an ongoing breeding program by the Inventor in Etten-Leur, The Netherlands. The objectives of the breeding program were to improved cultivars of strawberries with white fruit.

'BBB PO 01' arose from open pollination in spring of 2007 between a number of cultivars and varieties of *Fragaria* with white colored fruit and the seeds pooled and sown for evaluation. 'BBB PO 01' was selected as a single unique plant from the resulting seedling in spring of 2008. The exact parentage is unknown, however the parent plants are thought to be 'Annablanca' and 'Louis Gathier' (both unpatented) based on the characteristics of the new cultivar.

Asexual reproduction of the new cultivar was first accomplished by stolon cuttings by the Inventor in Etten-Leur, The Netherlands in 2008. Repeated propagation has shown that the unique characteristics of 'BBB PO 01' are stable and reproduced true to type in successive generations.

BRIEF SUMMARY OF THE INVENTION

The following traits have been repeatedly observed and represent the characteristics of the new *Fragaria*. These attributes in combination distinguish 'BBB PO 01' as unique and distinct from all other cultivars of *Fragaria* known to the Inventor.

1. 'BBB PO 01' exhibits white berries with red achenes.
2. 'BBB PO 01' exhibits berries that are firmer than is typical of other cultivars with white colored fruit.

3. 'BBB PO 01' exhibits berries that are very juicy.
4. 'BBB PO 01' exhibits berries are highly aromatic with a perfume-like fragrance.
5. 'BBB PO 01' exhibits berries with a pleasing flavor.

'BBB PO 01' differs from its probable parent plants in the following characteristics: 'BBB PO 01' differs from both 'Annablanca' and 'Louise Gathier' in having berries that are firmer, much juicier, and in having better aroma and flavor. 'BBB PO 01' also differs from 'Annablanca' in lacking a second crop in summer and in having more consistent fruit shape. 'BBB PO 01' also differs from 'Louise Gathier' in not having a mealy texture, and in being female. 'BBB PO 01' can also be compared to the cultivar 'Weisse Ananas' (not patented). 'BBB PO 01' differs from 'Weisse Ananas' in having berries that that have better aroma and flavor, in being juicier, in being not as mealy in texture, and in being female.

BRIEF DESCRIPTION OF THE DRAWING

The accompanying color photographs depict the characteristics of two year-old plants of 'BBB PO 01' as grown outdoors in a 4.7-liter container in Etten-Leur, The Netherlands. The colors in the photographs are as close as possible with the digital photography and printing techniques utilized and the color codes in the detailed botanical description accurately describe the colors of the new *Fragaria.*

The photograph in FIG. 1 illustrates a typical plant of 'BBB PO 01' in bloom.

Figure 1:
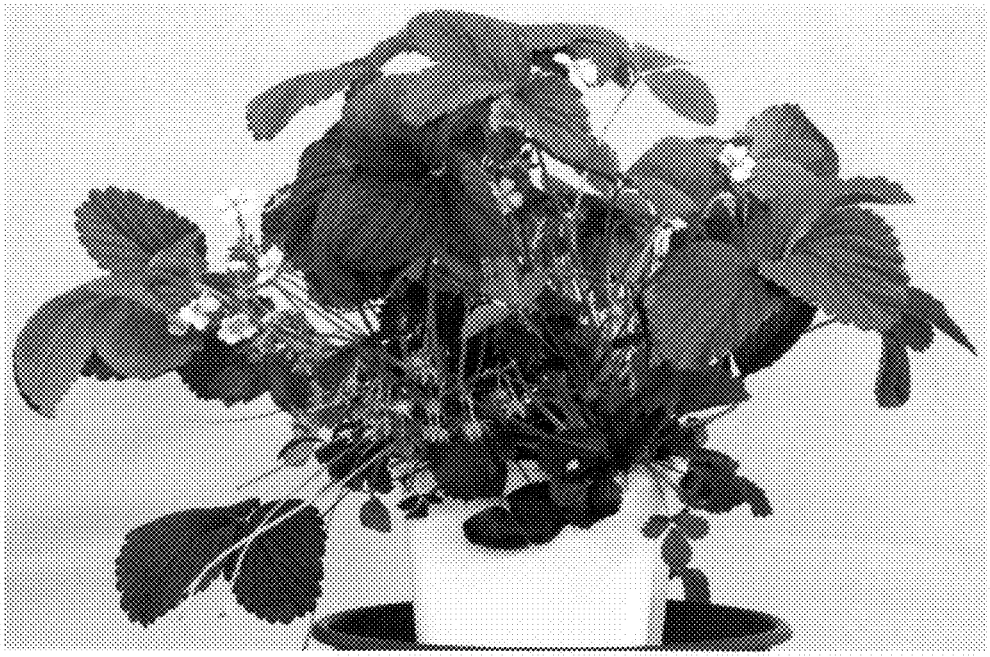
Figure 2:
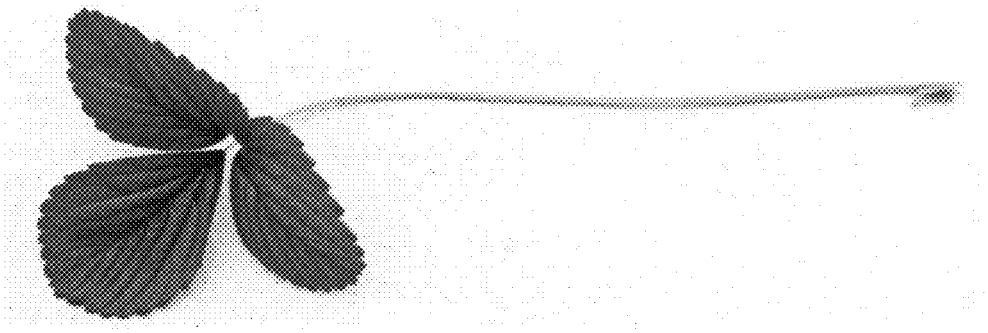

The photograph in FIG. 2 provides a close-up photo of a leaf of 'BBB PO 01'.

Figure 3:
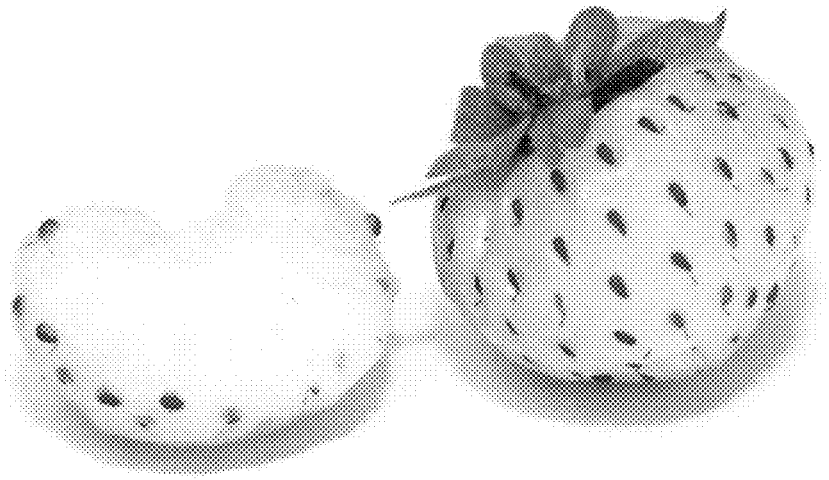

The photograph in FIG. 3 provides a close-up of the fruit of 'BBB PO 01'.

Figure 4:
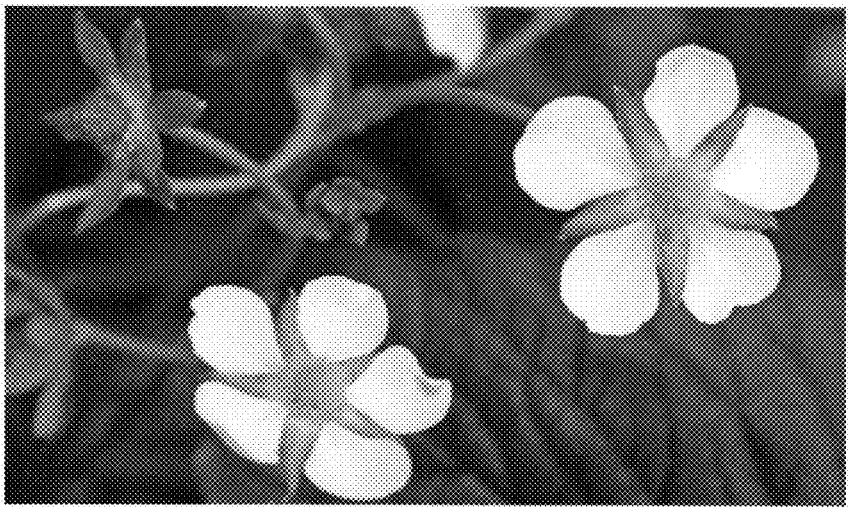

The photograph in FIG. 4 provides a close-up of the flowers of 'BBB PO 01'.

DETAILED BOTANICAL DESCRIPTION

The botanical data describing was collected on two year-old plants of 'BBB PO 01' as grown outdoors in a 4-liter container in Etten-Leur, The Netherlands. The characteristics may vary in detail depending on variations in conditions such as temperature, day-length, light intensity, soil types, and water and fertility levels as 'BBB PO 01' was not tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Commenced about the 3rd week in May in The Netherlands.

*Plant type.*—Herbaceous perennial.

*Plant habit.*—Upright and mounded, stoloniferous.

*Height and spread.*—Reaches about 55 cm in width and 33 cm in height.

*Cold hardiness.*—U.S.D.A. Zone 3.

*Environmental stresses.*—Berries may be susceptible to rain damage.

*Diseases resistance.*—Good tolerance to *Phytophthora cactorum* has been observed (not resistant).

*Root description.*—Fibrous.

*Propagation.*—Rooting of stolons.

*Growth rate.*—Vigorous.

*Stem description.*—Acaulescent.

*Stolon description.*—An average of 60 cm in length and 3 mm in diameter, 144B to 145A in color.

Foliage Description:

*Leaf division.*—Three leaflets.

*Leaf arrangement.*—Basal.

*Leaf attachment.*—Petiolate.

*Leaflet shape.*—Broadly obovate to broadly elliptic or rounded.

*Terminal leaflet size.*—Average of 11.7 cm in length and 8.9 cm in width.

*Leaflet margins.*—Serrate, average of 9 teeth per side on terminal leaflet.

*Angle of terminal leaflet to petiole.*—40° from vertical.

*Leaflet base.*—Broadly acute to short acuminate.

*Leaflet apex.*—Acute.

*Leaflet profile.*—Flat to slightly cupped upward.

*Leaflet interveinal blistering.*—Moderately strong.

*Leaflet venation.*—Pinnate, upper surface; 144B to 144C, lower surface; a color between 145A and 145B.

*Leaflet surface.*—Very sparsely pubescent and moderately glossy on upper surface, glaucous on lower surface with pubescence on veins and interveinal areas.

*Leaflet color.*—Upper surface N137A, lower surface 191A to 191B.

*Petiole.*—Round in shape, upper side flattened, average of 30.7 cm in length and 4 mm in diameter, pubescent surface, 144B in color.

*Petiolules.*—Round in shape, average of 1.0 cm in length and 2 mm in width, pubescent surface, 144B in color.

Flower description:

*Inflorescence.*—Compound cyme.

*Inflorescence length.*—Average of 11 cm (excluding peduncle).

*No. of flowers per cyme.*—Average of 13.

*Flower position relative to foliage.*—Beneath level of foliage.

*Flower diameter.*—Average of 3.2 cm, first flowers to open have an average diameter of 6 cm.

*Calyx.*—Position even to slightly reflexed, average of 2.3 cm in diameter.

*Sepals.*—Lanceolate, an average of 1 cm in length and 3 mm in width, puberulent on upper and lower surface, 138B on upper and lower surface, truncate base, acuminate apex.

*Petals.*—Average of 5, average of 1.4 cm in length and 1.25 cm in width, not touching, color NN155D on upper and lower surface, glabrous on upper and lower surface.

*Peduncle.*—144B in color, pubescent surface, average of 14.8 cm in length and 3 mm in diameter.

*Pedicel.*—144B in color, pubescent surface, average of 2.3 cm in length and 1.5 mm in diameter.

*Pistils.*—Average of 120, average of 1 mm in length, 151B to 151C in color at anthesis.

*Stamens.*—No stamens present.

Fruit description:

*Shape.*—Oblate (consistent).

*Length.*—Average of 2.1 cm in length and 2.6 cm in width.

*Surface.*—Relatively smooth.

*Calyx position.*—Impressed.

*Diameter of calyx relative to fruit diameter.*—Slightly smaller.

*Adherence of calyx.*—Strong.

*Glossiness.*—Even.

*External color (skin).*—A blend of 158C and 160D, can become flushed with 62D as it matures in summer.

*Internal color.*—NN155A with core area NN155C to NN155D.

*Evenness of color of skin.*—Even.

*Evenness of color of flesh.*—Slightly lighter near core.

*Fruit acidity.*—Medium to strong.

*Fruit sweetness.*—Very sweet.

*Fruit fragrance.*—Very aromatic, perfume-like.

*Fruit firmness.*—Medium, but firmer than is typical for cultivars with white colored fruit.

*Season of harvest.*—June bearing in The Netherlands, no fall bearing.

*Achene color.*—A color between 44A and 45A.

*Insertion of achenes.*—Deeply inserted.

*Achene size.*—1.8 mm in length and 0.8 mm in width.

It is claimed:

1. A new and distinct cultivar of *Fragaria* plant named 'BBB PO 01' as herein illustrated and described.

* * * * *